United States Patent [19]

Akaba et al.

[11] Patent Number: 4,537,480
[45] Date of Patent: Aug. 27, 1985

[54] MOTOR-DRIVEN SUBJECTIVE PHOROMETER

[75] Inventors: Hayao Akaba; Takeshi Yamada; Masahiro Jinbo, all of Tokyo, Japan

[73] Assignee: Hoya Lens Corporation, Tokyo, Japan

[21] Appl. No.: 500,069

[22] Filed: Jun. 1, 1983

[30] Foreign Application Priority Data

Jun. 25, 1982 [JP] Japan ................................ 57-109451

[51] Int. Cl.³ ............................................... A61B 3/02
[52] U.S. Cl. ................................................... 351/235
[58] Field of Search ................................ 351/234, 235

[56] References Cited

U.S. PATENT DOCUMENTS

| | | | |
|---|---|---|---|
| 3,969,020 | 7/1976 | Lynn et al. | 351/237 |
| 4,192,582 | 3/1980 | Aoki et al. | 351/234 |
| 4,385,813 | 5/1983 | Klein et al. | 351/235 |
| 4,436,390 | 3/1984 | Aoki | 351/234 |

Primary Examiner—Rodney B. Bovernick
Attorney, Agent, or Firm—Sprung, Horn, Kramer & Woods

[57] ABSTRACT

A new subjective phorometer which can be a desk-type one in which all the measuring means are set on the desk plate and all the procedures for measuring vision data of eyes are carried out by control switches on the desk, and all the data measured are displayed digitally on a monitor, and printed out.

The subjective phorometer comprises (1) the same measuring elements as conventional subjective phorometers, (2) a number of pulse motors, electro-magnetic clutches having a double-shafts mechanism, and direct current motors for driving the measuring elements and a number of sensors for detecting the zero position of the measuring elements, (3) a central processing unit and control switches for control driving of the pulse-motors, electro-magnetic clutches, and direct current motors, and (4) a monitor for displaying digitally the vision data measured, and (5) a printer for printing the data.

1 Claim, 7 Drawing Figures

MOTOR-DRIVEN SUBJECTIVE PHOROMETER

BACKGROUND OF THE INVENTION

1. Field of the Invention

This invention relates to a motor-driven subjective phorometer.

2. Description of the Prior Art

In prior subjective phorometers, the rotary motion of their every plate having a series of lenses (hereinafter referred to as lenses-plate) has been carried out by means of a knob connected directly or in gearing to the lenses-plate, and rising and falling one eye head, changing pupillary distance, and converging left eye head and right eye head have also been carried out by knobs connected in gearing thereto, so that the knobs have been attached separately in different positions and the data measured therewith must have been read in separated scales and displaying boards.

SUMMARY OF THE INVENTION

An object of this invention is to provide a motor-driven subjective phorometer in which all the measuring means can be driven only by a group of control switches gathered in a central panel, and all the data measured can be displayed digitally in a monitor and printed as required, and the data possessed previously or from other instruments such as objective phorometer and so on can be inputted thereto only by the group of control switches.

This invention relates to a motor-driven subjective phorometer which comprises a system for carrying out, by means of each pulse-motor through gears, the clockwise or counterclockwise controlled rotation of a spherical lenses-plate having a series of spherical lenses having respectively a different spherical power divided in a small dioptral steps, a toric lenses-plate having a series of toric lenses having respectively a different cylindrical power divided in a small dioptral steps, and a lecos plate, and the clockwise or counterclockwise controlled rotation of same cylinder axes of all the toric lenses of the toric lenses-plates, a system for carrying out, by means of each electromagnetic clutch having a double-shafts mechanism, the intermittent controlled rotation of a spherical lenses-plate having a series of spherical lenses having respectively a different spherical power divided in a large dioptral steps together with the spherical lenses-plate in the small dioptral steps, and of a toric lenses-plate having a series of toric lenses having respectively a different cylindrical power divided in a large dioptral steps together with the toric lenses-plate in the small dioptral steps, a system for carrying out, by means of each direct current motor through gears, the rising and falling motion of one side plate to which the lenses-plates are set, the convergence of right side plate and left side plate to which the lenses-plates are set, and the inward or outward sliding motion of the right side plate and left side plate, a system for carrying out, by means of control-switches through a central processing unit, all the controlled driving of said pulse-motors, electro-magnetic clutches, and direct current motors, and a system for displaying digitally in a monitor all the data measured by the systems controlled and printing out, as required, the same data.

DETAILED DESCRIPTION OF THE PREFERRED EMBODIMENTS

According to this invention, the subjective phorometer can be a desk-type one in which all the measuring elements are set on the desk plate and all the procedures for measuring vision data of eyes are carried out by control switches on the desk, and all the data measured are displayed digitally on a monitor, and printed out.

In this invention, elements for measuring vision data of eyes such as right and left eye heads consisting respectively of two spherical lenses-plates, two toric lenses-plates, and accessory lenses plate, an element for rising and falling the one eye head, an element for the convergence of left eye head and right eye head, and an element for adjusting pupillary distance, and so on are not different from those of other conventional ones, but the means for driving these elements and for displaying the data measured are completely different from those. The right eye head and left eye head are the symmetrically same, so that suffice it to say about one eye head.

Figure 1A:
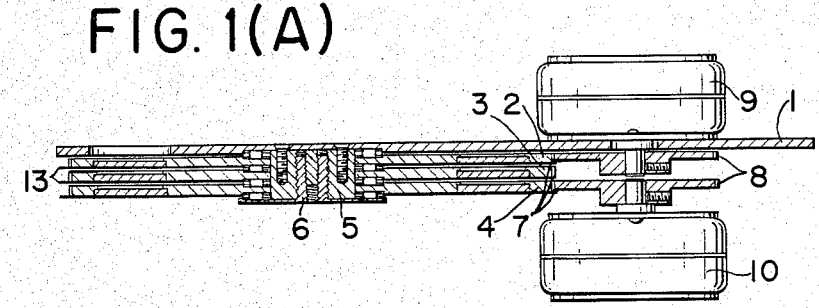
FIG. 1(A) and (B) are side views of a means for driving the two spherical lenses-plates, and a means for driving an accessory lenses plate, all of which are the ones of right eye head of a subjective phorometer of this invention. (A) represents a means for driving the spherical lenses-plate including a series of spherical lenses having respectively a different spherical power divided in a small dioptral steps, and (B) represents a means for driving spherical lenses-plate including a series of spherical lenses having respectively a different spherical power divided in a large dioptral steps.
Figure 1B:
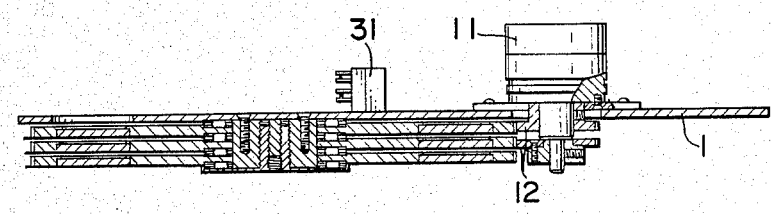
Figure 2A:
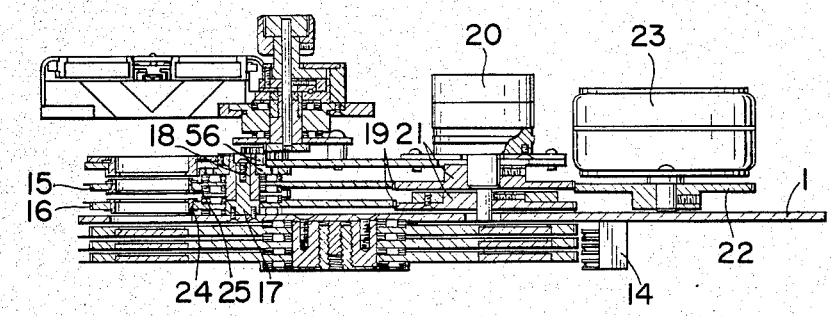
FIG. 2 (A) and (B) are side views of a means for driving two toric lenses-plates of right eye head of a subjective phorometer of this invention. (A) represents a means for driving the toric lenses-plate including a series of toric lenses having respectively a different cylindrical power divided in a small dioptral steps and a means for driving the toric lenses-plate including a series of toric lenses having respectively a different cylindrical power divided in a large dioptral steps, and (B) represents a means for driving all the cylinder axes of the toric lenses of the two toric lenses-plates.
Figure 2B:
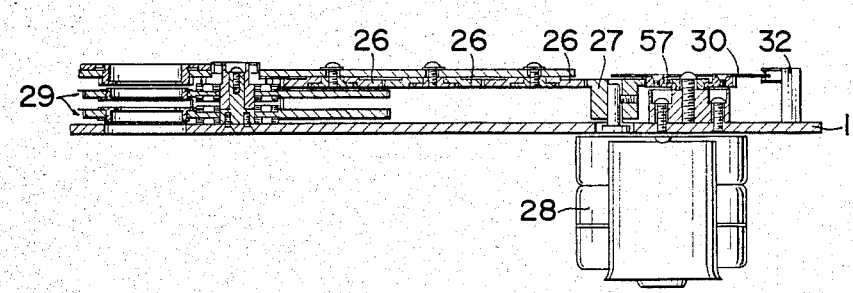

FIG. 1 and FIG. 2 are side views of means for driving the elements of right eye head. In FIG. 1 (A), 1 is a setting plate. A lenses-plate 2 having a circular series of spherical lenses having a different spherical power divided in 0.25 diopter steps, a lenses-plate 3 having a circular series of spherical lenses having a different spherical power divided in 3.00 diopters steps, and accessory lenses plate 4 having lenses necessary for measuring various kinds of vision data are respectively inserted into each fixing axle 5 of the setting plate 1, and are protected not to be detached from the fixing axel 5 by each setting screw 6.

Each plate of 2, 3, and 4 rotates around the axle 5, and has each gear 7 at the circumference of them, and the gear 7 of plate 2 engages with the gear 8, fixed to the shaft of pulse motor 9, and the gear 7 of accessory lenses plate 4 engages with gear 8 fixed to the shaft of pulse motor 10.

FIG. 1 (B) is a side view of an electro-magnetic clutch for rotating lenses-plate 3 as required, in which 11 is an electro-magnetic clutch having a double shafts mechanism, in which the gear 12 fixed to the shaft of the clutch 11 engages with the gear 7 of lenses-plate 2 and with the gear 7 of lenses-plate 3.

Each plate of 2, 3, and 4 has, at a position of each circumference, a shielding plate 13 which serves to detect the zero position of each plate in cooperation with each optical sensor 14 [is shown in FIG. 2 (A)] which is fixed to setting plate 1 in correspondence with each shielding plate 13.

FIG. 2 (A) is a side view of a means for driving two toric lenses-plates. FIG. 2 (B) is a side view of a means for driving cylinder axes of all the toric lenses of the two toric lenses-plates. A lenses-plate 15 is a toric lenses-plate having a circular series of five toric lenses having respectively a different cylindrical power divided in 0.25 diopter steps. A lenses-plate 16 is a toric lenses-plate having a circular series of toric lenses having respectively a different cylindrical power divided in 1.25 diopters steps. Plate 15 and 16 are respectively inserted rotatably into an axle 17 and gears 25, both of which are fixed to setting plate 1, being protected respectively by setting screw 18 and gears 56 not to be detached therefrom. Lenses-plate 15 and 16 have, at each circumference, each gear 19 which engages with gear 21 attached to an electro-magnetic clutch 20 which has a double shafts mechanism, and the gear 21 engages with a gear 22 attached to the shaft of a pulse motor 23.

Each lens in the series of toric lenses arranged in lenses-plate 15 and 16 is all set in a ring 24 which has a gear at the circumference, and the gear of each ring engages with one central gear 25 which engages with gear 56 and a joining gear 26 which engages with gear 27 attached to a pulse motor 28.

Each of plates 15 and 16 has, at each circumference, a shielding plate 29 which serves to detect the zero position of each plate of 15 and 16 by an optical senser 31 shown in FIG. 1 (B) attached to setting plate 1.

Each plate of 15 and 16 also has, at a gear 57 which engages with gear 27, a shielding plate 30 which serves to detect the zero position of the cylinder axes of all the toric lenses by an optical senser 32 attached to setting plate 1.

Figure 3:
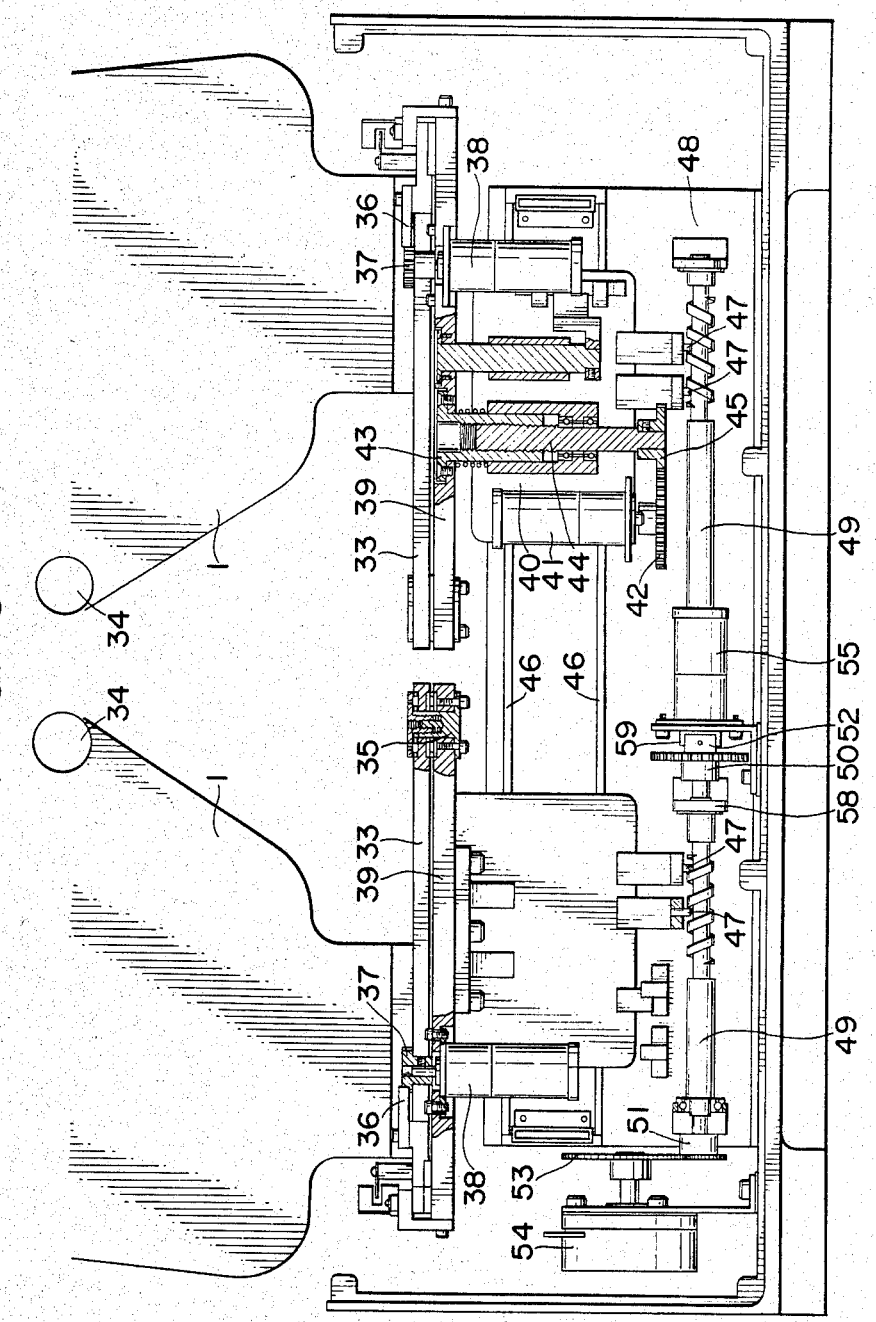
FIG. 3 is a front view of a means for the convergence of two plates for right and left eyes, each plate having all the spherical and toric lenses-plates fixed thereto, a means for rising or falling one eye head, and a means for adjusting pupillary distance, of a subjective phorometer of this invention.

FIG. 3 is a front view of a means for converging setting plate 1, a means for rising and falling one eye head i.e., a setting plate 1, and a means for adjusting pupillary distance. All the means is assembled in one case which is fixed on a desk. The case has two horizontal setting boards 39 for left and right eye, both of which are slidably mounted on the case by a means hereinafter being illustrated. Each of setting boards 39 has, at each opposite end, an axle 35 into which a convergence plate 33 is rotatably inserted at the one end thereof, so that the convergence plate 33 can be rotated at the center of axle 35. Each of the convergence plates 33 has the setting plate 1 which is screwed up vertically in parallel to plate 33 at the another end thereof. Setting plate 1 has a window 34 for measuring vision data whose center is on the center line of axle 35. Convergence plate 33 also has a gear 36 fixed to the end having setting plate 1, the gear 36 engaging with a gear 37 attached to a shaft of a direct current motor (DC-motor) 38 fixed to setting board 39. Rotary motion of both convergence plates 33, i.e., convergence of both setting plates 1 is carried out by the rotation of both DC-motors 38. Each of setting boards 39 also has a sliding plate 40 which is fixed thereto and slides on a rail 46 fixed to a base 48 by its sliding bearings. Each of sliding plates 40 has two rotatable pins 47 which are fixed at the under portion of 40 and are moved to both directions by the rotation of a leading screw 49, so that sliding plate 40 slides on rail 46 by the rotation of leading screw 49, which is set by flanges 58 at the both sides to base 48 fixed to the case, and both leading screws 49 are joined each other by a flexible joint 59. To leading screw 49 are attached a gear 50 which engages with a gear 52 of a DC-motor 55, and a gear 51 which engages with a gear 53 attached to a shaft of a senser 54 for showing pupillary distance. The sliding plate 40 for left eye shown in the right side in FIG. 3 has a mechanism for rising and falling one eye head, in which a gear 42 attached to a DC-motor 41 fixed to sliding plate 40 engages with a gear 45 attached to a vertical screw 44 engaged with a screw which is made inside the wall of a cylinder 43 fixed vertically to setting board 39, so that the rising and falling motion of cylinder 43 i.e., the rising and falling motion of setting board 39 or setting plate 1 is carried out by the rotation of DC-motor 41. In FIG. 3, drawing of a number of bolts and pins for attaching many other assemblies is omitted.

Figure 4:
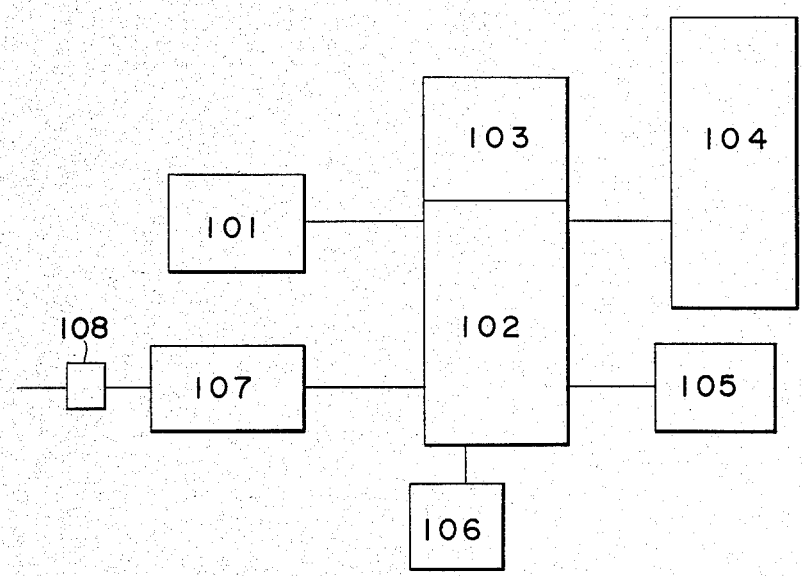
FIG. 4 is a block diagram of a subjective phorometer of this invention.

FIG. 4 is a schematic block diagram showing all the elements of an apparatus of this invention. In it 101 is a control switch board, 102 is a basic board for input and output, 103 is a basic board for central processing unit (hereinafter referred to CPU), 104 is a part for measuring vision data, 105 is a monitor, 106 is a printer, 107 is an electric source unit, and 108 is a breaker. In the part for measuring 104 there are employed eight pulse motors, four DC-motors, twelve zero position sensors, and four electromagnetic clutches. Operation of said driving means can be controlled via input-output board 102 and CPU board 103 by control switches of 101 on the desk, so that various kinds of vision data of patients can be obtained only by operation of the switches, and all the data can be digitally displayed in monitor 105 on the desk, and if necessary, can be printed out by printer 106 on the desk.

Figure 5:
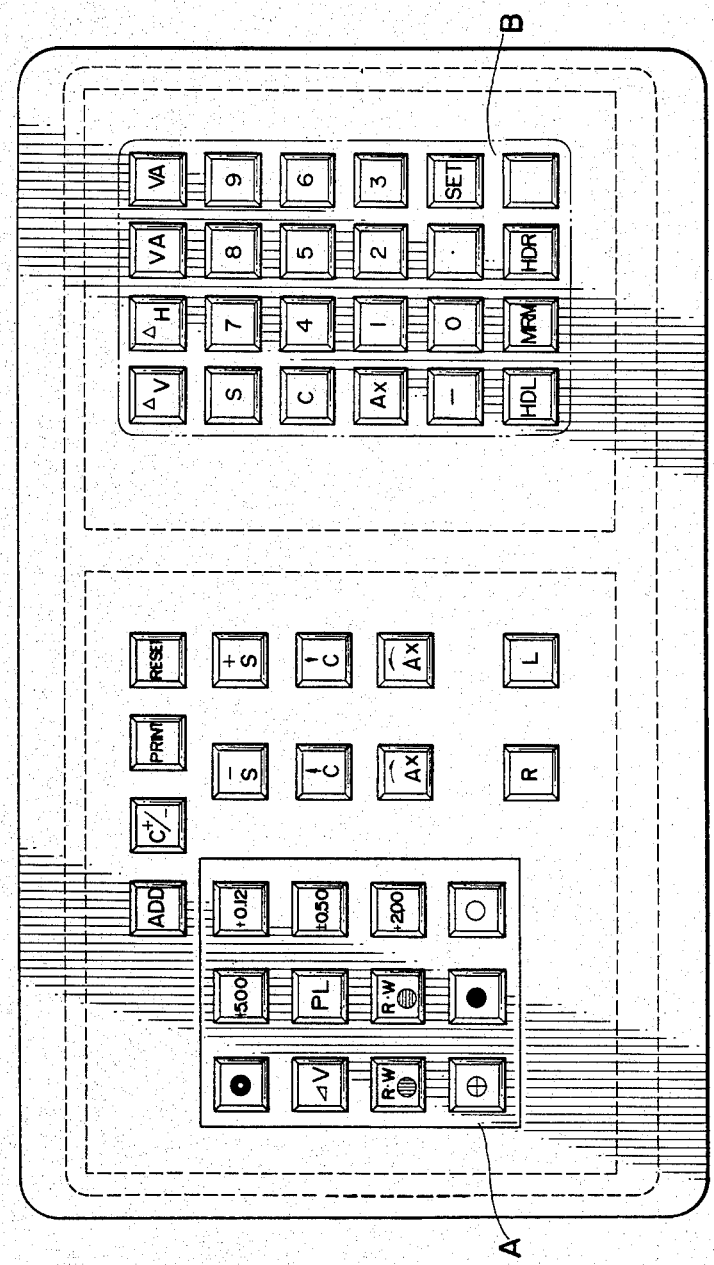
FIG. 5 is a plan view of a control switch panel of a subjective phorometer of this invention.

FIG. 5 is a plan view of a control switch board. In FIG. 5, there are not seen the switch for rising and falling one eye head and the switch for adjusting pupillary distance that are prepared in the part for measuring, but the switches of course may be prepared in the board of FIG. 5.

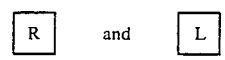

are switches for deciding for the control switches to be applied to either right eye head or left eye head.

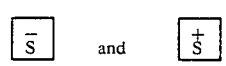

are switches for rotating either clockwise or counterclockwise the pulse motor 9 connected to spherical lenses-plate 2. Input from the switch

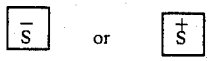

gives a signal to input-output board 102, whereas a definite number of pulses are simultaneously given to input-output board 102 from CPU board 103 in which micro-computer is enclosed, so that the pulse motor 9 is driven. One time pushing of switch

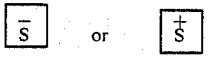

makes lenses-plate 2 rotate by the minimum diopter (0.25 d) pitch, and continuing the pushing makes lenses-plate 2 continue to rotate at a constant speed until the pushing is ended. At the position of just one before one rotation of lenses-plate 2 is completed during the pushing operation, current is introduced to electro-magnetic clutch 11, so that lenses-plate 2 and lenses-plate 3 are rotated simultaneously, and the current is off after one pitch rotation of lenses-plates 2 and 3. The electro-magnetic clutch 11 has a double shafts, either of which is freely rotated independently when the current is being cut off, but the double shafts are rotated together like one shaft when the current is introduced.

Switch

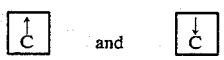

is the one for rotating toric lenses-plates. The motion which is conducted by pushing the switches is almost the same as the motion in the case of the switches

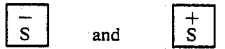

but toric lens can has a cylindrical power of only minus diopter, so that the arrow signs ↑, ↓ are employed. Simultaneous rotation of toric lenses-plate 15 and 16 is conducted by electro-magnetic clutch 20 like the spherical lenses-plate 2 and 3. Pushing switch

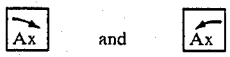

gives a number of pulses to pulse motor 28, rotating the cylinder axes of all toric lenses of toric lenses-plate 15 and 16 simultaneously to a same direction. The motion conducted by pushing the switch is the same as in the switches

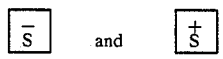

that one pitch rotation corresponds to one pushing, and continuation of pushing makes continuation of rotation at a constant speed until the pushing is ended.

Pushing a switch in the block A in FIG. 5 makes the CPU board 103 judge a necessary number of pulses, giving a signal to pulse motor 10, and rotating accessory lenses plate 4. Each switch in the block A corresponds to each function which is included in ordinary accessory lenses plate so that

is a switch representing a cross-line for measuring P.D. which is used in setting pupillary distance.

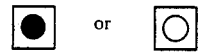

is a switch for closing or opening the measuring window 34.

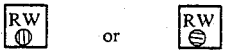

is a switch for Mardox which is used for measuring heterophoria.

is a switch for Retinoscopy which is used for measuring retinoscope objectively at a distance of 50 cm.

is a switch for supplementary prism, and

is a switch for polaroid lenses which is used for binocular test.

is a switch for fixed crossed-cylinder test for measuring hyperpoia which is used for measuring addition diopters for near working.

is a switch for pin hole which is used for checking amblyopia.

is a switch for supplementary spherical lenses which is used for measuring spherical power of up to +20 D.

[ +0.12 ]

is a switch for supplementary spherical lenses for intermediate power.

[ ADD ]

is a switch which is used for addition diopters necessary for near working, and is pushed to impress direct current to DC-motor 38 for convergence, converging the convergence plates inward by a necessary angle, simultaneously impressing DC-voltage to DC-motor 55 for measuring pupillary distance, and making the heads move few millimeter inward from the pupillary distance for far working.

[ C +/− ]

is a switch for C sign transposition,

[ PRINT ]

is a switch for printing vision data.

Switches in block B in FIG. 5 are supplementary ones which are used for inputting data previously measured.

[ ΔV ] and [ ΔH ]

are switches used for inputting vertical prism power or horizontal prism power.

[ VA ] and [ [VA] ]

are used for inputting vision power without glasses, and vision power with glasses.

[ S ], [ C ], [ Ax ], [ − ], [ 0 ] ~ [ 9 ], [ SET ], and [ . ]

are switches which are used to rotate lenses-plates in order to set appropriate lenses in front of patient's eyes when vision data of patient's eye glasses are previously known. For example, if S=1.00 D, C=0.50 D, and Ax=100°, switches are pushed in the order of

[ S ][ − ][ 1 ][ . ][ 0 ][ 0 ][ C ][ − ][ 0 ][ . ][ 5 ]

[ 0 ][ Ax ][ 1 ][ 0 ][ 0 ][ SET ].

Electric power inputted by pushing these switches enters to input-output board, and then to CPU board where are calculated the number of pulses to be given to pulse motor 9 in order to rotate spherical lenses-plate, the number of pulses to be given to pulse motor 23 in order to rotate toric lenses-plate, and the number of pulses to be given to pulse motor 28 in order to rotate the cylinder axes, and these numbers of pulses calculated are given to respective pulse motors for setting each the lenses-plate and the cylinder axes. Switches of

[ HDL ] , [ MRM ] and [ HDR ]

are the ones for inputting data measured by other instruments such as lensmeter, objective phorometer, etc. other than the subjective phorometer of this invention. If a certain one of these switches is pushed, the data is inputted to CPU board, the number of pulses required being calculated, the number being given to the pulse motor, and the lenses-plate and the cylinder axes being set.

In an example of this invention, there are attached in the cabinet of measuring the switch for giving a DC-voltage to DC-motor 41 for rising and falling one eye head, and the switch for giving DC-voltage to DC-motor 55 for adjusting pupillary distance, moving two heads to inward or outward direction. These switches can be of course included in the switch board of FIG. 5.

All the data such as ones from every lenses-plates which are controlled by main switches of the switch board mentioned above, ones inputted from supplementary switches of block B, and ones from other instruments can be displayed digitally in a monitor on the desk. And the data in the monitor can be printed out by a high speed printer, if the switch of

[ PRINT ]

is pushed. After measuring being finished,

[ RESET ]

switch is pushed, so that all the measuring means return to their zero positions for being ready to next measurement.

What is claimed is:

1. In a subjective phorometer having two eye heads, each eye head having a first rotatable spherical lens plate, a second rotatable spherical lens plate, a first rotatable toric lens plate, a second rotatable toric lens plate and a rotatable accessory lens plate, the improvement comprising: means on each eye head for rotating the first spherical lens plate and the accessory lens plate comprising a first D-C motor for each lens plate and gear means engaging the motors and plates; means on each eye head for rotating the second spherical lens plate comprising a first electromagnetic clutch with a double shaft mechanism for engaging the gear means for the first spherical lens plate or the accessory plate to rotate therewith; means on each eye head for rotating the first and second toric lens plates comprising a second D-C motor, a second electromagnetic clutch, gear means for alternatively engaging the first and second toric lens plates to effect rotation by the second D-C motor, a third D-C motor and gear means for effecting rotation the two toric lens plates together by the third motor; means for raising and lowering one eye head comprising a fourth D-C motor and gear means engaging the one eye head and the fourth motor; means for sliding the two eye heads towards and away from each other comprising a fifth D-C motor and gear means engaging the two eye heads with the fifth motor; means for rotating each eye head for converging motion comprising a sixth motor and gear means for each eye head to engage same with the sixth motor; first control switches settable to correspond to vision data; second control switches for effecting desired movement of the lens plates; central processing means receptive of the vision data from the first switches and for controlling the motors and electromagnetic clutches in response to the second switches; a monitor for digitally displaying vision data; and a printer for printing out vision data.

\* \* \* \* \*